(12) United States Patent
Ferguson et al.

(10) Patent No.: US 7,798,014 B2
(45) Date of Patent: Sep. 21, 2010

(54) METHOD AND APPARATUS FOR TESTING COMPOSITE MATERIALS

(75) Inventors: Robert Ferguson, Bristol (GB); Matthew Jevons, Bristol (GB)

(73) Assignee: Airbus UK Limited, Bristol (GB)

( * ) Notice: Subject to any disclaimer, the term of this patent is extended or adjusted under 35 U.S.C. 154(b) by 11 days.

(21) Appl. No.: 12/142,847

(22) Filed: Jun. 20, 2008

(65) Prior Publication Data

US 2009/0007692 A1    Jan. 8, 2009

(30) Foreign Application Priority Data

Jul. 6, 2007    (GB)    ................................. 0713047.9

(51) Int. Cl.
*G01N 3/08* (2006.01)
(52) U.S. Cl. .......................................... 73/831; 73/856
(58) Field of Classification Search ........... 73/760–761, 73/856–860
See application file for complete search history.

(56) References Cited

U.S. PATENT DOCUMENTS

| | | | | |
|---|---|---|---|---|
| 3,708,745 A | * | 1/1973 | McMaster et al. | ........... 324/727 |
| 3,757,204 A | * | 9/1973 | Hyde | .......................... 324/321 |
| 3,885,424 A | | 5/1975 | Ryckman et al. | |
| 4,142,402 A | * | 3/1979 | Mattioli et al. | ............. 73/61.62 |
| 4,541,287 A | * | 9/1985 | Roper | ......................... 73/827 |
| 4,639,997 A | * | 2/1987 | Brull | ....................... 29/407.01 |
| 4,895,750 A | | 1/1990 | Pratt | |
| 4,917,462 A | * | 4/1990 | Lewis et al. | ................. 359/368 |
| 5,220,401 A | * | 6/1993 | Milosevic et al. | ........... 356/246 |
| 5,284,063 A | | 2/1994 | Newell | |
| 5,528,942 A | * | 6/1996 | Baratta | ........................ 73/856 |
| 5,816,530 A | * | 10/1998 | Grube | .......................... 244/1 R |
| 6,370,919 B1 | * | 4/2002 | Kossat et al. | ................... 65/381 |
| 6,644,099 B2 | * | 11/2003 | Bell | ........................... 73/35.14 |
| 2005/0067084 A1 | | 3/2005 | Kagan et al. | |

OTHER PUBLICATIONS

UK Search Report for GB0713047.9 dated Oct. 8, 2007.

* cited by examiner

*Primary Examiner*—Max Noori
(74) *Attorney, Agent, or Firm*—Lowe Hauptman Ham & Berner LLP

(57) ABSTRACT

A test coupon has a waisted central section from which respective load introduction sections extend, each load introduction section having a pair of divergent load introduction surfaces extending from a respective curved surface of the central section. Test apparatus includes a test coupon as described above and a plurality of angled pivotable load introduction blocks such that the test coupon may self-align during application of a load.

18 Claims, 4 Drawing Sheets

METHOD AND APPARATUS FOR TESTING COMPOSITE MATERIALS

RELATED APPLICATIONS

The present application is based on, and claims priority from, British Application No. 0713047.9, filed Jul. 6, 2007, the disclosure of which is hereby incorporated by reference herein in its entirety.

BACKGROUND OF THE INVENTION

Composite laminated materials, such as Fibre Reinforced Plastics (FRPs) often demonstrate significantly lower tensile strength when loaded perpendicular to the laminations, i.e. in the through-thickness direction, than when loaded in the plane of the laminations. It is therefore desirable to obtain accurate mechanical properties for the tensile strength of such laminated materials when loaded in the through-thickness direction.

A first known test method to determine the through-thickness tensile strength of laminated materials is the "curved beam" approach. In this method a load is applied to an angled or C-section coupon (test element) and the resulting through-thickness tensile strength is calculated from elasticity equations for a curved beam segment with cylindrical anisotropy. For laminated FRPs the results obtained through this method are only valid if the reinforcing fibres run continuously along the coupon. Disadvantages of this method include a significant sensitivity to flaws and variations in the test material, the results may be influenced by interaction between interlaminar shear stresses and through-thickness tensile stresses, giving a low apparent through-thickness tensile strength result, the test coupons must be manufactured to a dedicated L-shaped geometry, which means that in most cases the coupons cannot be extracted directly from candidate materials, and this method does not allow true through-thickness tensile strength data to be generated for materials containing reinforcement in more than one direction, such as FRPs containing woven fabric.

A second known test method is the "direct pull" approach, in which end blocks are bonded to opposite faces of a test coupon and pulled to give a direct through-thickness tensile strength reading. The coupons for this method can be extracted directly from any sufficiently thick laminate. Disadvantages of this method include the results are dependent on obtaining a good bond between the coupon and the end blocks and are very sensitive to alignment of the end blocks during bonding and the alignment of the grips of the apparatus used to apply the load (load frame). The bonding of the end blocks to some materials, for example thermoplastics, can be difficult and can result in premature coupon failure.

SUMMARY OF THE INVENTION

According to a first aspect of the present invention there is provided a test coupon having a waisted central section from which respective load introduction sections extend, each load introduction section having a pair of divergent load introduction surfaces extending from a respective surface of the central section.

Preferably, the load introduction surfaces are angled flat surfaces and the surface of the central region is a curved surface. Preferably, the included angle of each load introduction surface is less than the included angle formed by a tangent to the radius of the curved surface of the central section at the point of transition from a load introduction surface to the curved surface.

Preferably the included angle of each load introduction surface is in the range of 15° to 40° and more preferably is in the range of 26° to 27°.

The longitudinal axis of the test coupon may extend through the load introduction sections and central section and the test coupon preferably has a laminated structure, the laminations being substantially perpendicular to the longitudinal axis.

According to a second aspect of the present invention there is provided a test apparatus comprising a test coupon according to the first aspect of the present invention and a plurality of load introduction blocks, each load introduction block having a first surface arranged to be placed in contact with a load introduction surface of the test coupon.

The first surface preferably has a profile corresponding to the profile of the load introduction surface and each load introduction block may further comprise a second curved surface substantially opposite the first surface.

The test apparatus may further comprise a test jig arranged to receive the test coupon and the load introduction blocks and arranged to be connected to a load application device, the apparatus being arranged such that, in use, each load introduction block may be pivotally engaged by the test jig.

Preferably the load introduction blocks comprise a first surface having a profile corresponding to the profile of the load introduction surface and a second curved surface substantially opposite the first surface and the test jig comprises at least one angled surface arranged to be in contact with the curved surface of one of the load introduction blocks.

The angled surfaces of the test jig may be arranged to be approximately parallel with the load introduction surfaces of the test coupon when the test coupon is located within the test jig.

According to a further aspect of the present invention there is provided a method of testing the tensile strength of a material, the method comprising the steps of forming a test coupon according to the first aspect of the present invention from said material, engaging the sides of the test coupon via the load introduction surfaces of the test coupon, and applying a tensile load to the coupon via the load introduction surfaces.

Preferably the step of forming a test coupon comprises extracting the coupon from a candidate material, such that the longitudinal axis of the coupon corresponds to the thickness direction of the candidate material.

The step of engaging the sides of the test coupon may comprise engaging opposing load introduction surfaces of the coupon with angled pivotable load introduction blocks such that the test coupon may self-align during application of a load.

BRIEF DESCRIPTION OF THE DRAWINGS

Embodiments of the present invention are described below, by way of illustrative example only, with reference to the accompanying figures, of which.

DESCRIPTION OF EMBODIMENTS OF THE INVENTION

Figure 1:
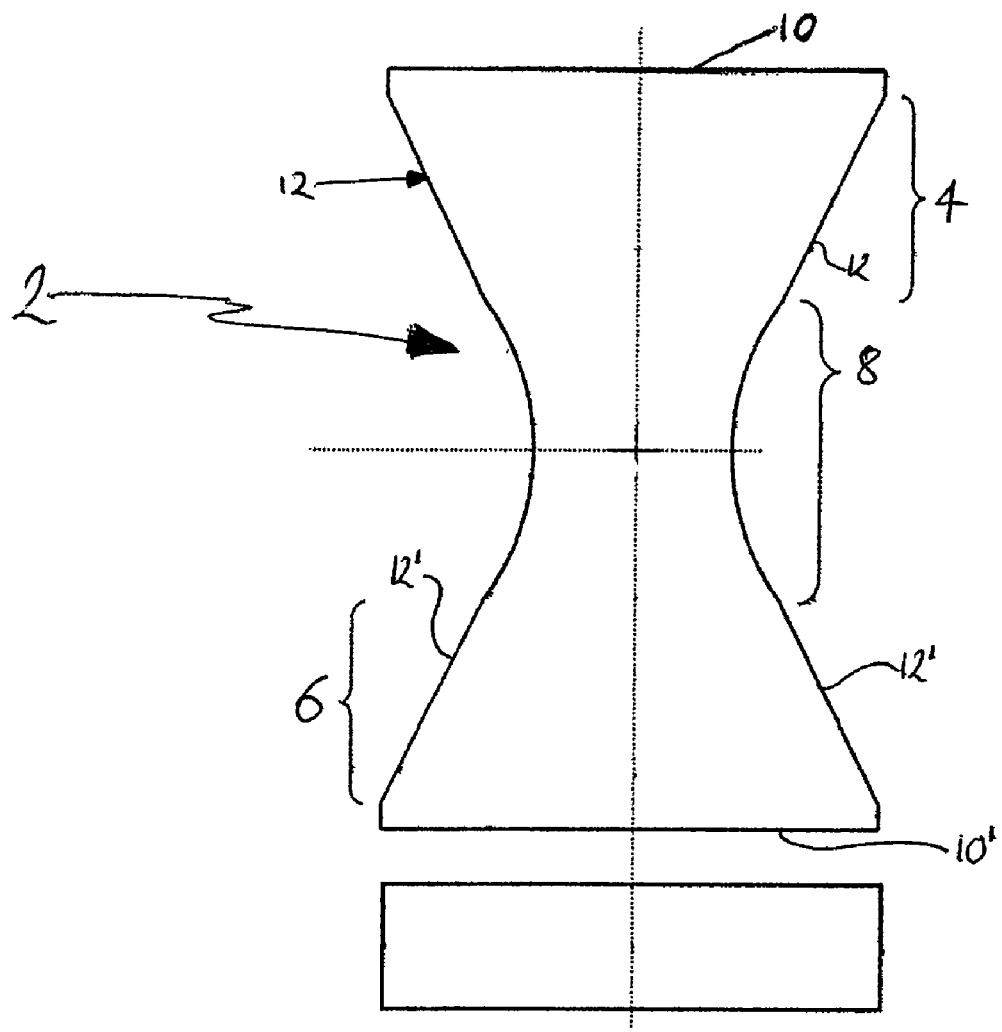
FIG. 1 illustrates a front and top elevation of a test coupon according to an embodiment of the present invention.

FIG. 1 illustrates a front and top elevation of a test coupon according to an embodiment of the present invention. The front elevation shows a two-dimensional 'hourglass' shape, with the coupon having a constant thickness, as indicated by the rectangular top elevation. The coupon 2 comprises generally of three regions; first and second load introduction regions 4,6 at either end of the coupon and a gauge section 8 adjoining each load introduction region. Each of the first and second load introductions regions 4,6 have a generally trapezoidal shape orientated such that the longer of the parallel sides 10, 10' form the ends of the coupon and the shorter of the parallel sides adjoining the gauge section 8. The angled sides 12, 12' of each load introduction region form the load introduction surfaces to which the test loads are applied. As will be explained further below, the load introduction surfaces are specifically arranged to receive the test load. The load introduction surfaces ensure that the test load is distributed across the load introduction area. By virtue of the trapezoidal shape of the adjoining load introduction regions the gauge section is of reduced cross-section, which promotes failure at the centre of the coupon. The sides of the gauge section are radiused, such that they are curved.

Figure 2:
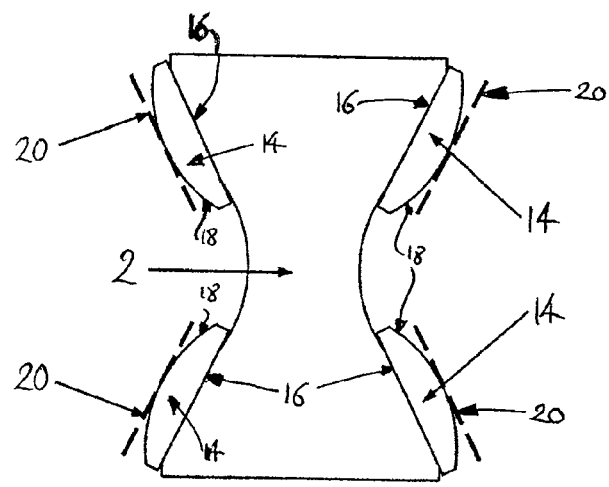
FIG. 2 illustrates a test coupon in combination with load transfer blocks according to an embodiment of the present invention.
Figure 3:
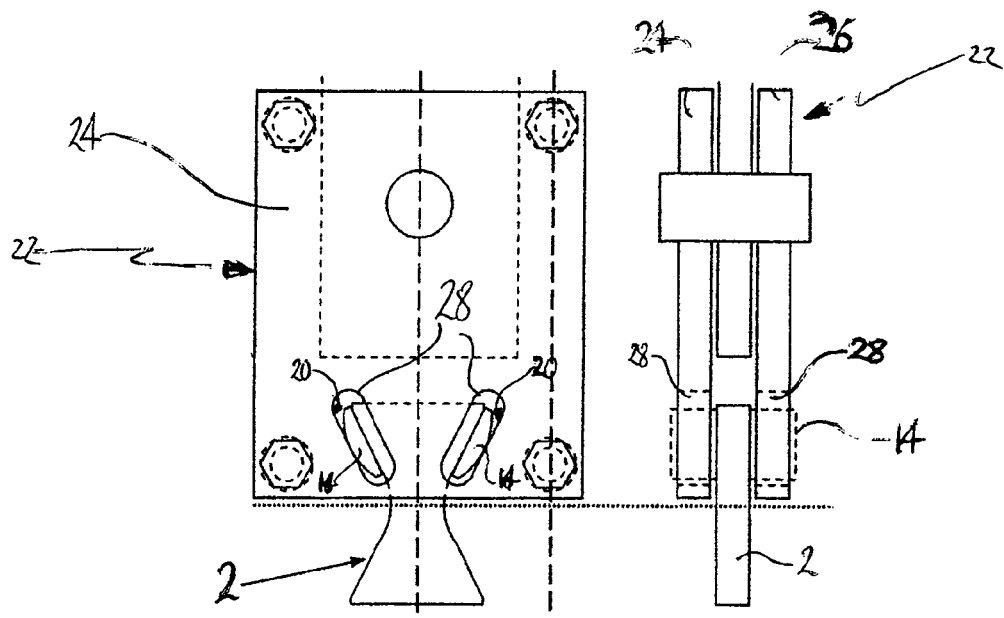
FIG. 3 illustrates a front and side elevation of a test jig loaded with a test coupon according to an embodiment of the present invention.

To apply the test load to the test coupons of embodiments of the present invention it is preferable to use load transfer blocks, as illustrated in FIG. 2. Each load transfer block 14 has a flat surface 16 that is arranged to bear against the flat, angled, surface of a corresponding load introduction region of a test coupon 2 and a curved surface 18 substantially opposite the flat surface 16 and arranged to bear against a flat surface 20 of a test jig. In preferred embodiments the load transfer blocks are curved in one dimension only i.e. they have a constant cross section along their length. A suitable test jig for use with the test coupons and load transfer blocks of the present invention is schematically illustrated in front and side elevations in FIG. 3. The jig 22 comprises two flat plates 24, 26 into which two angled slots 28 are formed. The plates 24, 26 are fastened to one another in a parallel and spaced apart relationship by means of a number of spacers (not illustrated) such that a test coupon 2 can be introduced into the space between the two plates. A load transfer block 14 is placed through each opposing pair of slots 28, each load transfer block being of a length equal to or greater than the width of the spaced apart plates. The test coupon 2 can thus rest on the flat surfaces of the load transfer blocks, as illustrated. The jig may be connected to a conventional load application apparatus by any suitable means such that a tensile load can be applied along the longitudinal axis of the test coupon. The jig may be formed as an integral part of a load application apparatus or may be a separate component. It will be appreciated that FIG. 3 only illustrates an upper jig assembly and that in practice an identical lower jig assembly mounted in mirror image to the upper jig assembly is required in which the lower part of the coupon is received in order to apply a load to both parts of the test coupon.

The geometry of the load transfer blocks 14 serves three functions. Firstly, the flat surface 16 spreads the load over the area of load introduction into the coupon to avoid point loads and consequent unfavourable stress distribution in the coupon that may lead to premature failure. Secondly, the curved sides 18 of the load transfer blocks 14 allows the coupon to be self-aligning when inserted into the jig 22, thus reducing the risk of load train misalignment. Thirdly, the curved sides also allow minor variations in the profile of the test coupons to be accommodated. Analysis has shown that if the load is introduced through fixed surfaces then variations in the shape of the coupon, even within typical machining tolerances, may give unacceptable local point loads leading to a premature failure of the test coupon. The curved sides of the load transfer blocks allow them to conform to the manufactured profile of the coupon and ensure even load introduction.

Figure 4:
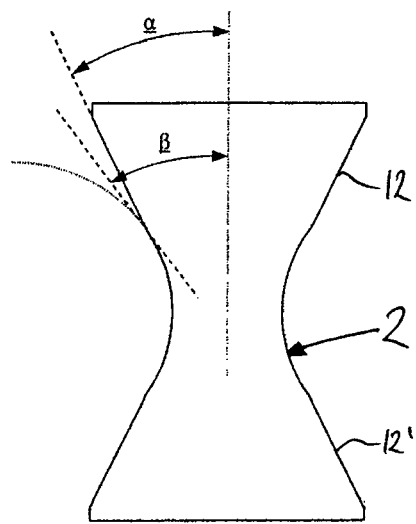
FIG. 4 illustrates the included angles α and β of a coupon according to an embodiment of the present invention and their inter-relation.

The geometry of the coupon directly affects the performance of the coupon during a load test. In particular, the angle of the load introduction surfaces 12, 12' strongly influence the failure mode of the coupon. Referring again to FIG. 1 and also in particular to FIG. 4, the angled load introduction surfaces 12, 12' of the coupon have an included angle $\alpha$ that in embodiments of the present invention is arranged to be less than the included angle $\beta$ formed by the tangent to the radius of the gauge section 8 at the point where the gauge section 8 joins the load introduction region 4. The transition from the flat load introduction surface 12, 12' to the curved gauge section 8 dictates where failure initiation of the coupon occurs. By setting $\alpha<\beta$ the risk of a local stress concentration occurring due to manufacturing errors at this transition point is significantly reduced. Additionally, the risk of the corner of a load transfer block 14 coming into contact with the actual gauge section 8 of the coupon 2 and introducing a point load is removed. For a constant coupon width, as the angle $\alpha$ is reduced towards 0° the lateral compressive load across the coupon (applied between the load introduction faces) increases and the shear stress (across the laminations) decreases. Conversely, as $\alpha$ increases towards $\beta$ the compressive load decreases whilst the shear stress increases. Thus $\alpha$ may be varied between 0° and $\beta$ depending on the requirements and properties of the candidate coupon material. For example, for typical aerospace grade FRP materials a value of $\alpha=26.6°$ has been found to optimise the stress fields in the coupon ends.

Figure 6:
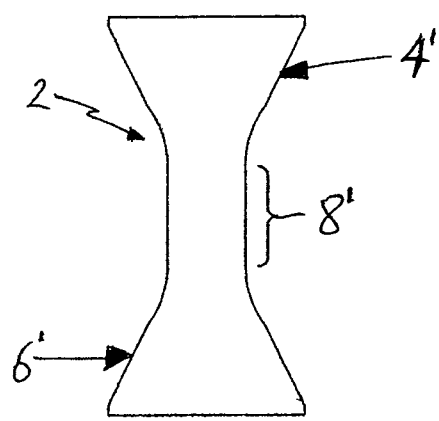
FIG. 6 illustrates a test coupon according to a further embodiment of the present invention with an extended gauge section.
Figure 5:
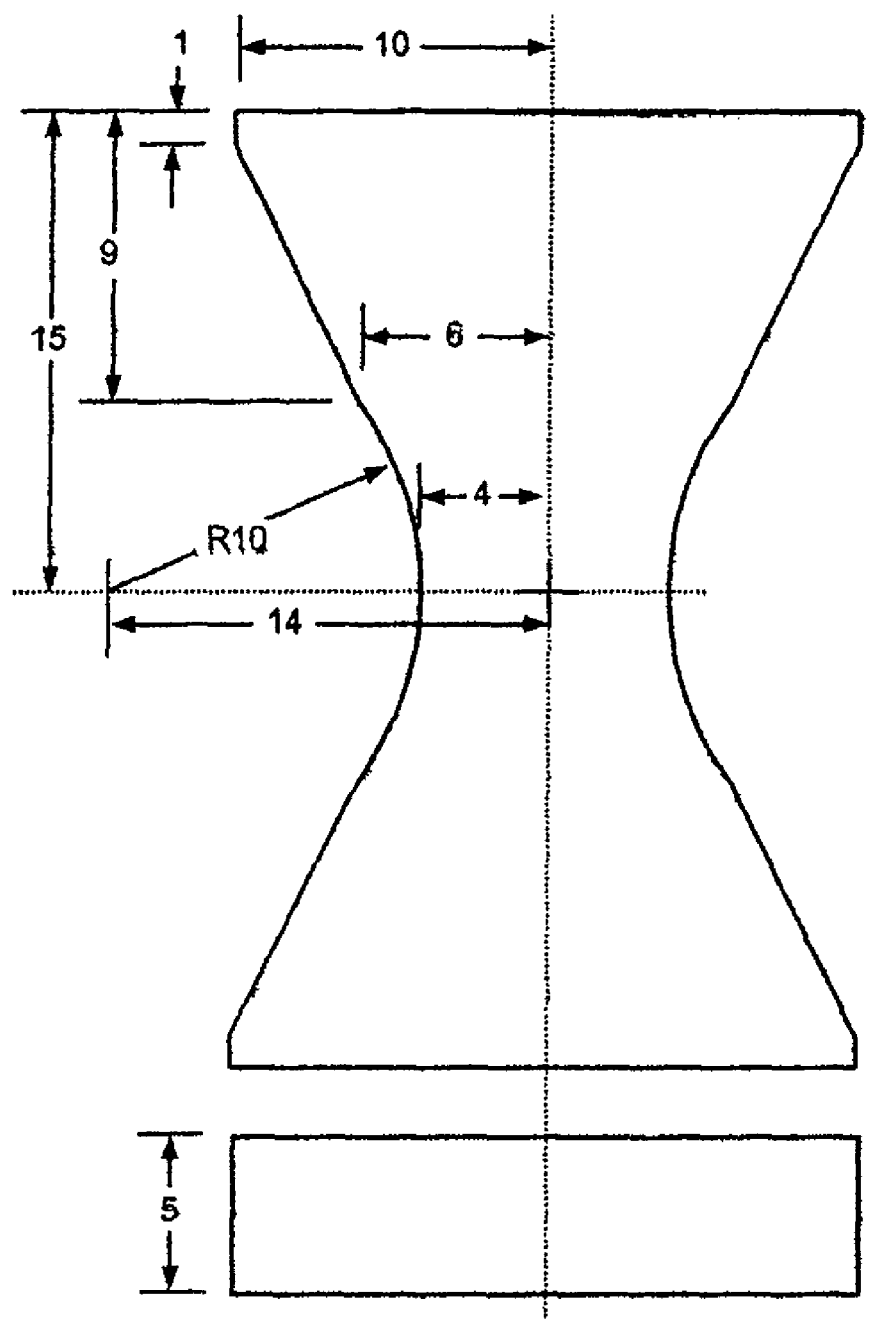
FIG. 5 illustrates a front and top elevation of a test coupon according to an embodiment of the present invention with nominal dimensions.

The nominal dimensions of a coupon according to one embodiment of the present invention are indicated in FIG. 5. However, the coupon dimensions can be scaled or adjusted and the thickness altered as required. For example, the gauge section of the coupon can be extended as illustrated in FIG. 6, such that the gauge section 8' has a radiused area adjacent to each load introduction region and then a parallel sided region between the radiused areas and can thus be used to obtain strain information during loading to allow the stress-strain response of the coupon material to be obtained.

Although the invention has been described above with reference to one or more preferred embodiments, it will be appreciated that various changes or modifications may be made without departing from the scope of the invention as defined in the appended claims.

For example, the skilled person will appreciate that the divergent shape of the pairs of load introduction surfaces advantageously ensures that a force may be applied to the load introduction area which will both grip the coupon and enable the tensile load to be introduced into the coupon. It will be understood that divergent is intended to mean that each pair of load introduction surfaces have a minimum separation proximal to the central region and extend to a maximum separation distal to the central region, for example proximal to the respective end of the test coupon. It will, therefore be appreciated that the it will be possible to provide a test coupon having load introduction surfaces that enable a tensile load to be applied via the sides of the test coupon but are not straight sided provided the geometry of the loading blocks substantially corresponds to that of the load introduction surfaces.

Furthermore, the skilled person will appreciate that the self-alignment of the load transfer blocks may be achieved by means other than by the provision of a curved face as in the preferred embodiment described above. For example, other means of pivotally connecting the transfer blocks to the test apparatus will be apparent to the skilled person, for example by a pin. Further, the blocks may be arranged to have freedom of rotation along more than one direction, for example by providing a load transfer block on which the curved surface 18 is curved in more than one dimension.

It will be appreciated that, while the invention may be used for testing of any material, embodiments of the invention may be particularly suitable for use with laminate materials such as fibre-reinforced plastics. For example, embodiments may help to ensure a distributed load introduction into the coupon to avoid point loads and consequent unfavourable stress distribution which could, for example, lead to local delamination.

The invention claimed is:

1. A test coupon, comprising:
   a waisted central section; and
   load introduction sections extending from said central section, each load introduction section having a pair of divergent load introduction surfaces extending from a respective surface of the central section and being arranged to receive a test load.

2. A test coupon according to claim 1, wherein the load introduction surfaces comprise angled flat load introduction surfaces and the surface of the central region comprises a curved surface, and the angle of each load introduction surface is less than the angle formed by a tangent to the radius of the curved surface of the central section at the point of transition from the load introduction surface to the curved surface.

3. A test coupon according to claim 2, wherein the angle of each load introduction surface is in the range of 15° to 40°.

4. A test coupon according to claim 3, wherein the angle of each load introduction surface is in the range of 26° to 27°.

5. A test coupon according to claim 1, wherein the longitudinal axis of the test coupon extends through the load introduction sections and central section and the test coupon has a laminated structure, the laminations being substantially perpendicular to the longitudinal axis.

6. Test apparatus, comprising:
   a test coupon according to claim 1; and
   a plurality of load introduction blocks, each load introduction block having a first surface arranged to be placed in contact with one of the load introduction surfaces of the test coupon.

7. Test apparatus, comprising:
   a test coupon having a waisted central section and load introduction sections extending from said central section, each load introduction section having a pair of divergent load introduction surfaces extending from a respective surface of the central section; and
   a plurality of load introduction blocks, each load introduction block having a first surface arranged to be placed in contact with the respective load introduction surface of the test coupon,
   wherein the first surface has a profile corresponding to the profile of the respective load introduction surface and each load introduction block further comprises a second, curved surface substantially opposite the first surface.

8. Test apparatus, comprising:
   a test coupon having a waisted central section and load introduction sections extending from said central section, each load introduction section having a pair of divergent load introduction surfaces extending from a respective surface of the central section; and
   a plurality of load introduction blocks, each load introduction block having a first surface arranged to be placed in contact with the respective load introduction surface of the test coupon; and
   a test jig arranged to receive the test coupon and the load introduction blocks and arranged to be connected to a load application device, the apparatus being arranged such that, in use, each load introduction block is pivotally engageable by the test jig.

9. Test apparatus according to claim 8, wherein the load introduction blocks comprise a first surface having a profile corresponding to the profile of the respective load introduction surface and a second, curved surface substantially opposite the first surface, and the test jig comprises at least one angled surface arranged to be in contact with the curved surface of one of the load introduction blocks.

10. Test apparatus according to claim 9, wherein said at least one angled surface of the test jig is arranged to be approximately parallel with one of the load introduction surfaces of the test coupon when the test coupon is located within the test jig.

11. A method of testing the tensile strength of a material, the method comprising:
    forming a test coupon according to claim 1 from said material;
    engaging the sides of the test coupon via the load introduction surfaces of the test coupon; and
    applying a tensile load to the coupon via the load introduction surfaces.

12. A method according to claim 11, wherein said forming comprises extracting the coupon from said material, such that the longitudinal axis of the coupon corresponds to the thickness direction of the material.

13. A method of claim 11, wherein said engaging comprises engaging opposing load introduction surfaces of the coupon with angled pivotable load introduction blocks such that the test coupon is self-alignable during application of the tensile load.

14. A method of claim 12, wherein said engaging comprises engaging opposing load introduction surfaces of the coupon with angled pivotable load introduction blocks such that the test coupon is self-alignable during application of the tensile load.

15. Test apparatus according to claim 6, wherein the first surface has a profile corresponding to the profile of the respective load introduction surface and each load introduction block further comprises a second curved surface substantially opposite the first surface.

16. Test apparatus according to claim 6 further comprising a test jig arranged to receive the test coupon and the load introduction blocks and arranged to be connected to a load application device, the apparatus being arranged such that, in use, each load introduction block is pivotally engageable by the test jig.

17. Test apparatus according to claim 16, wherein the load introduction blocks comprise a first surface having a profile corresponding to the profile of the respective load introduction surface and a second, curved surface substantially opposite the first surface, and the test jig comprises at least one angled surface arranged to be in contact with the curved surface of one of the load introduction blocks.

18. Test apparatus according to claim 17, wherein said at least one angled surface of the test jig is arranged to be approximately parallel with one of the load introduction surfaces of the test coupon when the test coupon is located within the test jig.

* * * * *